(12) United States Patent
Tortelli et al.

(10) Patent No.: US 7,612,242 B2
(45) Date of Patent: Nov. 3, 2009

(54) PROCESS FOR PREPARING FLUOROHALOGENETHERS

(75) Inventors: Vito Tortelli, Milan (IT); Pierangelo Calini, Milan (IT); Alberto Zompatori, Milan (IT); Emanuela Antenucci, Varese (IT)

(73) Assignee: Solvay Solexis S.p.A., Milan (IT)

( * ) Notice: Subject to any disclaimer, the term of this patent is extended or adjusted under 35 U.S.C. 154(b) by 95 days.

(21) Appl. No.: 11/634,145

(22) Filed: Dec. 6, 2006

(65) Prior Publication Data

US 2007/0149827 A1 Jun. 28, 2007

(30) Foreign Application Priority Data

Dec. 22, 2005 (IT) .......................... MI2005A2455

(51) Int. Cl.
*C07C 41/22* (2006.01)
(52) U.S. Cl. ....................... 568/685; 568/692
(58) Field of Classification Search ....................... None
See application file for complete search history.

(56) References Cited

U.S. PATENT DOCUMENTS

| 3,450,684 | A | | 6/1969 | Darby |
| 3,817,960 | A | | 6/1974 | Resnick |
| 3,896,179 | A | | 7/1975 | Resnick |
| 4,340,750 | A | | 7/1982 | Yamabe et al. |
| 4,418,232 | A | * | 11/1983 | Maurin, III ................ 570/228 |
| 4,515,989 | A | | 5/1985 | Ezzell et al. |
| 4,827,024 | A | | 5/1989 | Guglielmo et al. |
| 4,900,872 | A | | 2/1990 | Guglielmo et al. |
| 5,350,497 | A | | 9/1994 | Hung et al. |
| 5,646,223 | A | * | 7/1997 | Navarrini et al. ............. 526/247 |
| 6,255,536 | B1 | | 7/2001 | Worm et al. |

FOREIGN PATENT DOCUMENTS

EP 0 201 871 A1 11/1986
EP 1 352 892 A1 10/2003

OTHER PUBLICATIONS

Barbour et al., "*The Preparation of Organic Fluorine Compounds by Halogen Exchange*", Adv. Fluorine Chem., 3, 1963, pp. 194-201.
Vecchio et al., "*Studies on a Vapour-Phase Process for the Manufacture of Chlorofluoroethanes*," J. Fluorine Chem. 4, 1974, pp. 117-139.
DiLorto et al., "*The thermal addition of trifluoromethyl hypofluorite, CF3OF, to tetrachloroethene*", J. Fluorine Chem. 74, 1975, pp. 199-201.
Weyl, vol. E10 B2, pp. 125-161 , 2000.

* cited by examiner

*Primary Examiner*—Rosalynd Keys
(74) *Attorney, Agent, or Firm*—Arent Fox LLP

(57) ABSTRACT

A process for preparing fluorovinylethers having general formula:

$$R_fO-CF=CF_2 \qquad (IA)$$

wherein $R_f$ is a fluorinated or perfluorinated alkyl or cycloalkyl substituent; comprising the following reaction steps:
1) reaction of a hypofluorite;
2) dehalogenation or dehydrohalogenation of the fluorohalogenethers obtained in step 1) and obtainment of vinyl ethers;
3) fluorination with fluorine of the vinyl ethers and obtainment of fluorohalogenethers; and
4) dehydrohalogenation of the fluorohalogenethers and obtainment of the fluorovinylethers of formula (IV).

The compounds of formula (IA) can be used, for example, in the preparation of various polymers, such as fluorinated elastomers and fluorinated thermoprocessable semicrystalline polymers.

13 Claims, No Drawings

PROCESS FOR PREPARING FLUOROHALOGENETHERS

The present invention relates to a process for preparing fluorohalogenethers. More specifically the invention relates to fluorohalogenethers which by dehalogenation or dehydrohalogenation allow to obtain perfluorovinylethers. Still more specifically the present invention relates to a process for preparing perfluorovinylethers, preferably perfluoromethylvinylether and perfluoroethylvinylether with improved yields and selectivity, and using precursors not belonging to the chlorofluorocarbon (CFC) class and besides obtainable without expensive separation processes from hydrogenated by-products.

It is well known that CFCs, due to their impact on the ozone layer (ODP) and due to their high environmental impact (GWP) have been banned or limited by the Montreal protocols and subsequent modifications. In any case, in the few fields wherein they can still be used, it is necessary to avoid that CFCs are dispersed in the environment and thus their use is expensive from the industrial point of view.

As known, perfluorovinylethers are useful monomers for preparing various polymers, from fluorinated elastomers to fluorinated thermoprocessable semicrystalline polymers.

Processes for preparing perfluorovinylethers are known in the prior art. U.S. Pat. No. 3,450,684 relates to vinylethers of formula:

$$CF_2=CFO(CF_2CFX^0{}_fO)_{nI}CF_2CF_2X^0{}_I$$

wherein $X^0{}_I=F$, Cl, $CF_3$, H and nI can range from 1 to 20.

These compounds are obtained by starting from HFPO. The process is carried out in more steps according to the following scheme:

$$X^0{}_fCF_2CF_2O-(CFX^0{}_fCF_2O)_{nI-1}-CFX^0{}_fCOF + HFPO \longrightarrow$$
$$X^0{}_fCF_2CF_2O-(CFX^0{}_fCF_2O)_{nI}-CF(CF_3)COF$$
$$X^0{}_fCF_2CF_2O-(CFX^0{}_fCF_2O)_{nI}-CF(CF_3)COF + NaOH \longrightarrow$$
$$X^0{}_fCF_2CF_2O-(CFX^0{}_fCF_2O)_{nI}-CF(CF_3)COONa$$
$$X^0{}_fCF_2CF_2O-(CFX^0{}_fCF_2O)_{nI}-CF(CF_3)COONa \xrightarrow{212°C.}$$
$$X^0{}_fCF_2CF_2O-(CFX^0{}_fCF_2O)_{nI}-CF=CF_2$$

The yields of this process are low.

U.S. Pat. No. 3,817,960 relates to the preparation of perfluorovinylethers of formula:

$$CF_3O(CF_2O)_{n''}CF_2CF_2OCF=CF_2$$

wherein n" can range from 1 to 5.

The synthesis requires the preparation of an acylfluoride of formula:

$$CF_3O(CF_2O)_{n''}CF_2C(O)F$$

by TFE oxidation at low temperature in the presence of U.V. radiations or by electrochemical fluorination of the corresponding hydrogenated acylfluoride. Then the acylfluoride is reacted according to the following scheme:

$$CF_3O(CF_2O)_{n''}CF_2C(O)F + HFPO \xrightarrow{CsF}{Solv.}$$
$$CF_3O(CF_2O)_{n''}CF_2CF_2OCF(CF_3)COF$$

$$CF_3O(CF_2O)_{n''}CF_2CF_2OCF(CF_3)COF \xrightarrow{Na_2CO_3}{Solvent}$$
$$CF_3O(CF_2O)_{n''}CF_2CF_2OCF=CF_2$$

In this synthesis scheme the preparation of the starting acylfluoride from TFE is an expensive process from the industrial point of view. When the electrochemical fluorination is used, the yields are low due to the formation of by-products.

U.S. Pat. No. 3,896,179 relates to the separation of linear alkyl chain perfluorovinylethers from branched alkyl chain isomer perfluorovinylethers by thermal decomposition at temperatures in the range 300°-600° C. As a matter of fact branched isomers generally act as chain transfer agents giving polymers having poor mechanical properties. Therefore branched vinylethers are undesired when linear vinylethers are used for obtaining polymers.

U.S. Pat. No. 4,340,750 relates to the preparation of perfluorovinylethers of formula:

$$CF_2=CFOCF_2R^0{}_fX^1$$

wherein $R^0{}_f$ is a $C_1$-$C_{20}$ perfluoroalkyl optionally containing oxygen, $X^1$=H, Cl, Br, F, $COOR^0$, $CONR^0R'$ wherein $R^0$ is a $C_1$-$C_{10}$ alkyl group and R' represents H or a $C_1$-$C_{10}$ alkyl group.

In the preparation of these compounds an acylfluoride together with iodine and tetrafluoroethylene is used. In this process the final step of the alkaline acylfluoride pyrolysis is avoided. The synthesis scheme is the following:

$$X^1R^0{}_fCOF + C_2F_4 + I_2 + KF \xrightarrow{Solvent} X^1R^0{}_fCF_2OCF_2CF_2I$$
$$X^1R^0{}_fCF_2OCF_2CF_2I \xrightarrow{Zn}{Solvent} X^1R^0{}_fCF_2OCF=CF_2$$

The drawback of this process is that the deiodofluorination reaction (last step of the reaction) takes place with low yields.

U.S. Pat. No. 4,515,989 relates to the preparation of new compounds for the fluorovinylether synthesis. According to the patent the vinylether synthesis is improved by using a specific compound capable to decarboxylate easily. For the intermediate preparation fluoroepoxides are used, of formula:

$$X^3CF_2-CF-CF_2 \atop \diagdown O \diagup \qquad (1a)$$

wherein $X^3$ = Cl, Br

The reaction scheme is the following:

$$R_{fA}COF + X^3CF_2-CF-CF_2 \xrightarrow{CsF} R_{fA}CF_2OCF(CF_2X^3)COF$$
$$\diagdown O \diagup$$
$$R_{fA}CF_2OCF(CF_2X^3)COF \xrightarrow{Na_2CO_3/Solvent}{120°C.} R_{fA}CF_2OCF=CF_2$$

The drawback of this process is that the precursors for obtaining the fluoroepoxides (1a) are industrially hardly available.

U.S. Pat. No. 5,350,497 relates to the preparation of perfluoro-alkylvinylethers through the fluorination with fluorine of partially fluorinated hydrodichloroethers and subsequent dechlorination, according to the following scheme:

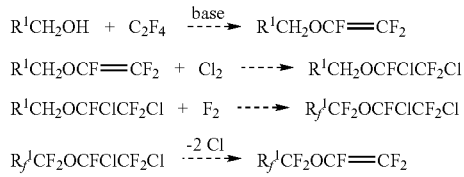

This process has the drawback that the fluorination step with fluorine takes place with not high yields and an excess of fluorine is employed to replace all the hydrogen atoms.

U.S. Pat. No. 6,255,536 describes a process wherein it is taken into account the synthesis of a hydrogenated precursor, which can also be partially halogenated, the precursor fluorination to form an acid derivative, which by alkaline pyrolysis is decomposed to perfluorovinylether. The scheme is the following:

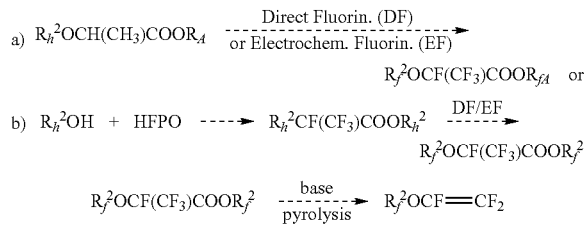

The fluorination step can be carried out by electrochemical fluorination or by fluorination with fluorine according to U.S. Pat. No. 5,488,142. The former reaction generally takes place with low selectivity and formation of undesired by-products. In the fluorination with fluorine industrially acceptable yields and productivity are not obtained. One operates indeed at high dilutions of the hydrogenated precursor and of the fluorine to control the heat generated by the reaction. Furthermore the fluorination with fluorine requires long reaction times, necessary for obtaining a complete fluorination of the compound. It is known that the fluorination of hydrogenated compounds is a very exothermic reaction which can cause the breaking of carbon-carbon bonds with formation of undesired by-products. See the book Fluorine Chemistry; A Comprehensive Treatment, in Kirk Othmer Encyclopedia, pages 242-259. Furthermore, to obtain a complete conversion, therefore to substitute all the hydrogen atoms of the precursor molecule, it is necessary to increase the temperature and therefore to adopt more drastic reaction conditions. This usually brings to a yield lowering in the useful product as there are secondary decomposition reactions.

EP 1,352,892 describes a process for preparing fluorinated vinylethers from acylfluorides, obtained by decomposition of fluorinated esters. The scheme is the following:

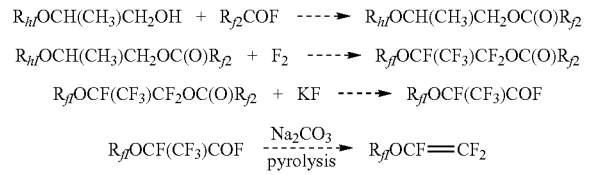

In the second step of the synthesis scheme the complete fluorination of the partially hydrogenated precursor esters is achieved obtaining the corresponding perfluorinated esters. This step of the complete fluorination of the partially fluorinated ester requires that the reaction is carried out for very long times, with several additions of a hydrogenated compound, for example benzene, to favour the total conversion of the ester. Contemporaneously the reaction temperature must be increased, for example from −10° C. up to room temperature. The productivity of this kind of fluorination is very low.

Processes for preparing fluorohalogen ethers by reacting hypofluorites with halofluorinated olefins are known in the prior art. U.S. Pat. No. 4,900,872 describes the synthesis of fluorohalogenethers by reaction between perfluoroalkyl hypofluorites, diluted in an inert solvent, and a halofluorinated olefin having formula $CA^IF=CA^{II}F$ wherein $A^I$ and $A^{II}$, equal to or different from each other, are Cl and Br. The olefin used in the syntheses described in the Examples of this patent is 1,2-dichloro-1,2-difluoroethylene (CFC 1112). The synthesis of said olefin is generally carried out by dehalogenation of the tetrachloro difluoro-ethane $CCl_2FCCl_2F$ (CFC 112) with metallic zinc in alcoholic solvent. See for example Houben Weyl, vol. E 10 B2, pages 125-161. The CFC 112 precursor used in this synthesis is a chlorofluorocarbon which, as said, falls within the Montreal protocols and its amendments on the reduction of the gas emissions destroying the ozone layer in the stratosphere. According to these protocols the CFC emissions must be gradually reduced in the time until they are then completely eliminated. Industrially CFC 112 was obtained as a component of a mixture of various chlorofluoroethanes, symmetric and asymmetric, mainly CFC 113 ($CF_2Cl$—$CFCl_2$) and CFC 114 ($CF_2Cl$—$CF_2Cl$).

The latter compounds were those of greater industrial interest as used as refrigerants and solvents. The synthesis methods of these chlorofluoroethane mixtures are for example reported in Adv. Fluorine Chem. 3 (1963), "The Preparation of Organic Fluorine Compounds by Halogen Exchange" pages 194-201, Fluorine Chem. 4 (1974), 117-139. Since it is no longer possible to use the CFC 113 and 114 compounds, also CFC 112 and thus CFC 1112 are industrially no longer available.

The need was felt to have available an industrial process to synthesize perfluoroalkylvinylethers with high yields and selectivity.

The Applicant has surprisingly and unexpectedly found a process overcoming the above technical problem.

An object of the present invention is a process for preparing perfluoroalkylvinylethers having general formula:

$$R_fO—CF=CF_2 \quad \text{(IA)}$$

wherein:

$R_f$ is a $C_1$-$C_3$, preferably $C_1$-$C_2$, perfluorinated substituent;

comprising the following steps:

1) reaction between a hypofluorite of formula RfOF, wherein Rf is as defined above, and an olefine of formula:

$$CY''Y=CY'Cl \quad \text{(II)}$$

wherein Y, Y' and Y", equal to or different from each other, are H, Cl, Br, with the proviso that Y, Y' and Y" are not contemporaneously hydrogen;

2) elimination from the fluorohalogenethers of formula (III) and (III') of halogen molecules (dehalogenation)/hydrohalogenic acid (dehydrohalogenation) wherein the halogen/halide ion is Cl or Br, and obtainment of vinyl ethers of formula:

$$RfO—CY_I=CY_{II}F \quad \text{(IV)}$$

wherein $Y_I$ and $Y_{II}$, equal to or different from each other, have the meaning of H, Cl, Br with the proviso that $Y_I$ and $Y_{II}$ are not both H;

3) fluorination with fluorine of the vinyl ethers (IV) and obtainment of fluorohalogenethers of formula:

$$Rf\text{O}\!-\!CFY_I\!-\!CF_2Y_{II} \qquad (I)$$

wherein $Y_I$, $Y_{II}$, equal to or different from each other, are Cl, Br, H with the proviso that $Y_I$ and $Y_{II}$ cannot be contemporaneously equal to H; Rf is as above;

4) elimination from the fluorohalogenethers of formula (I) of halogen/hydrohalogenic acid molecules wherein the halogen/halide ion is Cl or Br, and obtainment of vinyl ethers of formula:

$$Rf\text{O}\!-\!CF\!=\!CF_2 \qquad (IA).$$

In step 1) a mixture of fluorohalogenethers is generally obtained, of formula:

$$Rf\text{O}\!-\!CY''Y\!-\!CY'ClF \qquad (III)$$

$$Rf\text{O}\!-\!CY'Cl\!-\!CY''YF \qquad (III')$$

wherein Y, Y' and Y" have the above meanings; the compounds (III) and (III') being equal when the starting olefin (II) is symmetric.

In step 1) the reaction is carried out in liquid phase at temperatures from −130° C. to 0° C., preferably from −80° C. to −10° C.

The perfluoroalkyl hypofluorites with number of carbon atoms equal to or higher than 2 are known from U.S. Pat. No. 4,827,024. The trifluoromethyl hypofluorite is known in the art.

Organic solvents inert under the conditions utilized in step 1) can optionally be used.

This step can be carried out in various ways, for example in the reactor containing the olefin at the liquid state, optionally diluted with an inert solvent under the reaction conditions, the hypofluorite is fed, prepared in liquid or gaseous phase, diluted in a compound inert under the reaction conditions.

The olefins of formula (II) are preferably selected from the following: tetrachloroethylene, trichloroethylene, 1,2-dichloroethylene and 1,1-dichloroethylene.

In step 2) the dehalogenation (chlorine or bromine removal) of fluorohalogenethers (III) and (III') is, for example, carried out by reaction of said compounds with transition metals as zinc, copper, manganese or with metal couples as Zn/Cu, Zn/Sn, Zn/Hg, in the presence of solvents as, for example, hydrogenated protics as, for instance, alcohols, or hydrogenated ethers as, for example, glymes, dioxane, or dipolar aprotic solvents as, for example, DMF, DMSO.

In step 2) the dehydrohalogenation (HCl or HBr removal) of the fluorohalogenethers of formula (III) and (III') takes place, for example, by reacting these compounds with an inorganic base, preferably NaOH or KOH, or an organic base, preferably primary, secondary or tertiary alkyl or aryl amines. Liquid phase is generally used. The elimination reaction of hydrohalogenic acid in step 2) can optionally be carried out in the presence of a solvent, preferably aqueous or alcoholic. By using aqueous inorganic bases the reaction can be carried out in the presence of a quaternary ammonium or phosphonium salt as ammonium or phosphonium tetrabutyl, preferably chloride, ammonium or phosphonium trioctyl benzyl, preferably chloride, etc. Alternatively, or in admixture with the quaternary ammonium or phosphonium salts, other salts as, for example, sulphonium salts, can be used.

In the dehalogenation or dehydrohalogenation step 2) one generally operates at temperatures in the range 0°-150° C., preferably 25°-100° C.

In step 3) the fluorination reaction is carried out by addition of gaseous fluorine, optionally in the presence of an inert diluent as, for example, $N_2$, He, etc., to the compounds of formula (IV), liquid at the reaction temperature, by optionally using a solvent or a mixture of inert solvents being at the liquid state under the conditions in which step 3) is carried out.

In step 3) one generally operates at temperatures between −120° C. and 0° C., preferably −90° C. and −30° C.

The optional solvents usable in steps 1) and 3) are selected from the following: (per)fluoropolyethers, for example Galden®, (per)fluoroalkanes, for example from 3 to 10 carbon atoms, provided that they are liquid under the reaction conditions, hydrofluorocarbons (HFC), hydrochlorofluorocarbons (HCFC), chlorofluorocarbons (CFC), perfluoroamines, hydrofluoroethers or hydrofluoropolyethers, for example H-Galden® or mixtures thereof.

In step 4) the dehalogenation or elimination of chlorine or bromine from fluorohalogenethers of formula (I) is for example carried out by reaction of said compounds with transition metals as zinc, copper, manganese or with metal couples as Zn/Cu, Zn/Sn, Zn/Hg in the presence of solvents which can be either hydrogenated protics as alcohols, or hydrogenated ethers as glymes, dioxane, or dipolar aprotic solvents as DMF, DMSO.

In step 4) the dehydrohalogenation or elimination of HCl or HBr from the fluorohalogenethers of formula (I) takes place, for example, by reacting these compounds with an inorganic base, preferably NaOH or KOH, or an organic base, preferably primary, secondary or tertiary alkyl or aryl amines. One generally operates in liquid phase. The elimination reaction of hydrohalogenic acid in step 4) can optionally be carried out in the presence of a solvent, preferably aqueous or alcoholic. By using aqueous inorganic bases the reaction can be carried out in the presence of a quaternary ammonium or phosphonium salt as ammonium or phosphonium tetrabutyl, preferably chloride, ammonium or phosphonium trioctyl benzyl, preferably chloride, etc. Alternatively, or in admixture with quaternary ammonium or phosphonium salts, other salts as, for example, sulphonium salts can be used.

In the dehalogenation or dehydrohalogenation step 4) one generally operates at temperatures in the range 0°-150° C., preferably 25°-100° C.

In the process of the present invention the ratio between the reactants in the various steps is not critical.

In the process of the present invention the pressure is not critical and preferably one operates at atmospheric pressure.

The process of the present invention can be carried out in a discontinuous, semicontinuous or continuous way.

For example, with reference to step 3), the semicontinuous process can be carried out by feeding gaseous fluorine and the compound of formula (IV) in the reactor containing the solvent or the mixture of the reaction solvents.

In step 1) a continuous process can be used, wherein the gaseous hypofluorite and the compound of formula (II) are fed into the reactor, until reaching the steady state. In practice the reactants are fed into the reactor with known flow-rates, by continuously drawing the reaction mixture. The steady state is reached when the reactant and reaction product concentrations in the reactor are equal to the reactant and reaction product concentrations at the reactor outlet.

The compounds of formula (I), preparable with the process of the present invention, are for example the following: $CF_3O$—$CFCl$—$CF_2Cl$, $C_2F_5O$—$CFCl$—$CF_2Cl$, $C_3F_7O$—$CFCl$—$CF_2Cl$.

The compounds of formula (III) and (III') usable in step 2) are preferably those wherein Rf is $C_1$-$C_3$, still more preferably $C_1$-$C_2$ perfluoroalkyl.

Examples of these compounds are the following:

$CF_3O$—$CHCl$—$CFCl_2$, $CF_3O$—$CCl_2$—$CHClF$, $CF_3O$—$CCl_2$—$CCl_2F$, $CF_3O$—$CHCl$—$CHClF$, $CF_3O$—$CH_2$—$CCl_2F$, $C_2F_5O$—$CHCl$—$CFCl_2$, $C_2F_5O$—$CCl_2$—$CHClF$, $C_2F_5O$—$CCl_2$—$CCl_2F$, $C_2F_5O$—$CHCl$—$CHClF$, $C_2F_5O$—$CH_2$—$CCl_2F$, $C_3F_7O$—$CHCl$—$CFCl_2$, $C_3F_7O$—$CCl_2$—$CHClF$, $C_3F_7O$—$CCl_2$—$CCl_2F$, $C_3F_7O$—$CHCl$—$CHClF$, $C_3F_7O$—$CH_2$—$CCl_2F$.

Unexpectedly and surprisingly the process of the present invention allows to obtain in each single step high yields combined with high selectivity. Therefore the perfluoromethylvinylether and perfluoroethylvinylether are obtained with high yields and selectivity in comparison with the processes of the prior art. Furthermore the process of the present invention uses precursors not belonging to the chlorofluorocarbon (CFC) class and obtainable without expensive separation processes from hydrogenated by-products.

The olefins used in step 1) of the process of the present invention are commonly available on the market and economically cheap.

With the process of the invention, if desired, perfluoropropylvinylether can also be obtained, by using the propylhypofluorite in the first reaction step.

The following Examples illustrate with non limitative purposes the invention.

EXAMPLES

Example A

Synthesis of $CF_3OF$ 10 l/h of gaseous fluorine, 5 l/h of CO and 10 l/h of nitrogen are contemeporaneously allowed to flow in an AISI 316 steel pipe (inner diameter 2.17 mm and length 100 mm). The reaction is triggered by heating the gas mixing zone at 100° C. for some minutes. During the whole time the reactor is cooled by air circulation so that the temperature is lower than 300° C.; at the reactor outlet the temperature is 250° C. Under these conditions CO and $F_2$ are converted into $COF_2$ with a yield higher than 95% (determined by IR analysis of the outflowing gaseous mixture).

The gaseous mixture, after cooling at 100° C., is allowed to flow through a catalytic bed formed of 300 g of fine milled anhydrous CsF having particle size lower than or equal to 0.1 mm, mixed with 300 g of needle-shaped copper having diameter of 0.2 mm and length 6-7 mm. The catalyst is placed in a tubular reactor (inner diameter 55 mm, length 250 mm). The reaction temperature among gases is maintained at 100° C.

Under these conditions the $COF_2$ is converted into $CF_3OF$ with yield higher than 98%, determined by IR analysis of the outflowing mixture.

Example 1

Addition of $CF_3OF$ to Trichloroethylene 60.5 g of $CF_3OCFCl$—$CF_2Cl$ ether as solvent of the reaction and 4.35 g of trichloroethylene are introduced in a 50 cc glass reactor, equipped with mechanical stirrer. The reactor is then cooled to the temperature of −50° C. by cryogenic bath. Through a bubbling inlet 21.7 g of trichloroethylene (TCE) are fed into the reactor in 5 hours, by a pump. Contemporaneously, always through a bubbling inlet, 1.125 Nl/h of $CF_3OF$ diluted with helium in a molar ratio He/$CF_3OF$ of 1.6 and fed in a molar ratio $CF_3OF$/TCE equal to 1.5, are introduced.

At the end of the reaction 97.5 g of product are discharged. By the GLC/MS analysis a TCE conversion of 99.8% and a selectivity in the two reaction products $CF_3O$—$CHCl$—$CFCl_2$ and $CF_3O$—$CCl_2$-$CHClF$ equal to 96% are obtained.

Example 2

Dehydrochlorination of the $CF_3O$—$CHCl$—$CFCl_2$ and $CF_3O$—$CCl_2$—$CHClF$ Compounds Obtained in the Example 1

50 g of the compounds obtained in the Example 1 and 4.1 g of tetrabutylammonium hydroxide in aqueous solution at 40% by weight are introduced in a 250 ml four-necked reactor equipped with magnetic stirrer, dropping funnel, thermometer and water condenser. Under stirring 17 g of NaOH in aqueous solution at 20% are added, containing the exothermic heat at 34° C. with a bath of $H_2O$ and ice. When the soda addition is ended, the mixture is left under stirring at 34° C. for further 30 minutes. It is cooled at 20° C.: the final mixture shows two separate phases. The reaction mixture is poured in a separatory funnel separating 38.8 g of organic phase having a higher density, formed of the compound $CF_3OCCCl$=$CClF$ (chloro-methylvinylether, CVE), pure at 99% molar. Conversion 100%, yield 92%.

Example 3

Addition of Fluorine to CVE in a Discontinues Way 72.4 g of $CFCl_3$ as solvent and 8 g of chloromethyl-vinylether are introduced in the same reactor used in the Example 1, cooled at the temperature of −70° C. by a cryogenic bath. Through a bubbling inlet 1.0 Nl/h of $F_2$ diluted with nitrogen in molar ratio $N_2$/$F_2$ of 1.6 are fed. The fluorination is carried out for 10 minutes.

At the end of the reaction 80.7 g of product are discharged. The mixture is analyzed by GLC/MS. The CVE conversion is equal to 31.5%, the selectivity in $CF_3O$—$CFCl$—$CF_2Cl$ is 79.0%.

Example 4

Addition of Fluorine to CVE in a Semicontinuous Way

In the same reactor used in the Example 1, cooled at the temperature of −70° C. by cryogenic bath, 63.7 g of $CFCl_3$ are introduced. Through a bubbling inlet 2.0 Nl/h of $F_2$ diluted with nitrogen in a molar ratio $N_2/F_2$ equal to 1.6, and 9.28 g/h of CVE are fed. The fluorination is carried out for 4 hours.

At the end of the reaction 107.5 g of mixture are discharged, which is analyzed by GLC/MS. The CVE conversion is quantitative. The yield in $CF_3O$—$CFCl$—$CF_2Cl$ is 98.4%.

Example 5

Dechlorination of $CF_3OCCl_2CCl_2F$

The compound $CF_3OCCl_2CCl_2F$ is prepared by reacting tetrachloroethylene with methyl hypofluorite according to J. Fluor. Chem., vol. 74, 1995, 199-201.

80.0 g of zinc in powder, activated by washing with a 3 N HCl solution, 550 ml of DMF and 50 mg of KI, are introduced, under inert nitrogen atmosphere, in a 1 litre three-necked reactor, equipped with magnetic stirrer, dropping funnel, thermometer, connected through a vigreaux column and a water condenser to a cold trap maintained at the temperature of –75° C. The inner temperature is brought to 90° C. Then 102.0 g of $CF_3OCCl_2CCl_2F$ are dropwise added. When the addition is over, the mixture is left under stirring for one hour at 90° C. 62.8 g of CVE are collected in the cold trap. The CVE yield is equal to 83%.

Example 6

Addition of $CF_3CF_2CF_2OF$ to $CHCl=CHCl$

A solution formed of 62 g of $CHCl=CHCl$ and 300 g of $CFCl_3$ are introduced in a 350 ml glass reactor equipped with mechanical stirrer, cooled at the temperature of –90° C. by cryogenic bath. Through a bubbling inlet 1.8 Nl/h of $CF_3CF_2CF_2OF$, prepared according to U.S. Pat. No. 4,900,872, and 6.0 Nl/h of He are fed for 5 hours and 40 minutes.

By the GLC/MS analysis an hypofluorite conversion of 100% is drawn. By fractional distillation of the reaction raw product 33.9 g of adduct $CF_3CF_2CF_2OCHClCHClF$ are obtained with a yield, calculated on the fed hypofluorite, of 25%.

Example 7

Addition of $CF_3CF_2OF$ to $CHCl=CCl_2$ 40 g of $CF_2Cl$—$CFCl_2$ are fed in the same reactor used in the Example 1, cooled at the temperature of –70° C. by cryogenic bath. Through a bubbling inlet 0.76 Nl/h of $CF_3CF_2OF$, prepared according to U.S. Pat. No. 4,900,872, diluted with nitrogen (molar ratio $CF_3CF_2OF$/nitrogen 1/10) and contemporaneously 4.4 g/h of $CHCl=CCl_2$ are fed.

The reaction is carried out for 3 hours. The raw product (65.0 g) is analyzed by GLC/MS. The hypofluorite conversion is 100% and the selectivity in the two reaction products $CF_3CF_2O$—$CHCl$—$CFCl_2$ and $CF_3CF_2O$—$CCl_2$—$CHClF$ is equal to 61%.

The invention claimed is:

1. A process for preparing perfluoroalkylvinylethers having the general formula:

$$R_fO\text{—}CF=CF_2 \quad (IA)$$

wherein $R_f$ is a $C_1$-$C_3$, perfluorinated substituent;
comprising the following steps:
1) reaction of a hypofluorite of formula $R_fOF$, wherein $R_f$ is as above, with an olefin selected from the group consisting of: trichloroethylene; 1,2-dichloroethylene; and 1,1-dichloroethylene;
2) dehalogenation or dehydrohalogenation of the fluorohalogenethers obtained in step 1) and obtainment of vinyl ethers of formula:

$$R_fO\text{—}CY_I=CY_{II}F \quad (IV)$$

wherein $Y_I$ and $Y_{II}$ are selected from the group consisting of H, Cl, and Br with the proviso that one of $Y_I$ and $Y_{II}$ is H;
3) fluorination with fluorine of the vinyl ethers (IV) and obtainment of fluorohalogenethers of formula:

$$R_fO\text{—}CFY_1\text{—}CF_2Y_{II} \quad (I)$$

wherein $Y_I$, $Y_{II}$ and $R_f$ are as above; and
4) dehydrohalogenation of the fluorohalogenethers of formula (I) and obtainment of vinyl ethers of formula:

$$R_fO\text{—}CF=CF_2 \quad (IA).$$

2. A process according to claim 1, wherein step 1) is carried out in liquid phase at temperatures from –130° C. to 0° C., optionally in the presence of organic solvents.

3. A process according to claim 1 wherein in step 2), the dehalogenation is carried out with transition metals or with metal couples, in the presence of solvents selected from the group consisting of: hydrogenated protics, hydrogenated ethers, and dipolar aprotic solvents.

4. A process according to claim 1, wherein in step 2) the dehydrohalogenation is carried out with an inorganic or an organic base.

5. A process according to claim 4, wherein the dehydrohalogenation is carried out in the presence of a quaternary ammonium or phosphonium salt selected from the group consisting of: ammonium tetrabutyl, ammonium trioctyl benzyl, phosphonium tetrabutyl and phosphonium trioctyl benzyl.

6. A process according to claim 1, wherein step 2) occurs at temperatures in the range of 0°-150° C.

7. A process according to claim 1, wherein in step 3) the reaction is carried out by addition of gaseous fluorine, optionally in the presence of an inert diluent, to the compounds of formula (IV), liquid at the reaction temperature, by optionally using a solvent or a mixture of inert solvents being at the liquid state under the conditions in which step 3) is carried out.

8. A process according to claim 1, wherein step 3) occurs temperatures between –120° C. and 0° C.

9. A process according to claim 1, wherein in steps 1) and 3), solvents may optionally be used, wherein the solvents are selected from the group consisting of: (per)fluoropolyethers, (per)fluoroalkanes, HFC, HCFC, CFC, perfluoroamines, hydrofluoroethers or hydrofluoropolyethers, and mixtures thereof.

10. A process according to claim 1, wherein in step 4) the dehydrohalogenation is carried out with an inorganic or organic base.

11. A process according to claim 10, wherein the dehydrohalogenation is carried out in the presence of a quaternary ammonium or phosphonium salt selected from the group consisting of: ammonium tetrabutyl, ammonium trioctyl benzyl, phosphonium tetrabutyl and phosphonium trioctyl benzyl.

12. A process according to claim 1, wherein step 4) occurs at temperatures in the range 0°-150° C.

13. A process according to claim 1, carried out in a discontinuous, semicontinuous or continuous way.

* * * * *